United States Patent [19]

Patterson et al.

[11] 4,339,622
[45] * Jul. 13, 1982

[54] METHOD FOR PREPARING ETHYL BENZENE

[75] Inventors: John A. Patterson, Fishkill, N.Y.; Wheeler C. Crawford, Houston; James R. Wilson, Missouri City, both of Tex.

[73] Assignee: Texaco, Inc., White Plains, N.Y.

[*] Notice: The portion of the term of this patent subsequent to Aug. 7, 1996, has been disclaimed.

[21] Appl. No.: 1,244

[22] Filed: Jan. 5, 1979

Related U.S. Application Data

[63] Continuation of Ser. No. 952,763, Oct. 19, 1978, Pat. No. 4,163,761.

[51] Int. Cl.³ .............................................. C07C 5/52
[52] U.S. Cl. .................................................. 585/433
[58] Field of Search .......... 260/668 D, 668 R, 669 R; 585/445, 433

[56] References Cited

U.S. PATENT DOCUMENTS

| 2,438,041 | 3/1948 | Dutcher | 260/669 R |
| 3,903,185 | 9/1975 | Vogel et al. | 260/668 D |
| 4,036,901 | 7/1977 | Kawakami et al. | 260/669 R |
| 4,048,243 | 9/1977 | Ruckelshauss | 260/668 D |
| 4,163,761 | 8/1979 | Patterson et al. | 584/445 |

FOREIGN PATENT DOCUMENTS

| 41-9168 | 9/1966 | Japan | 260/669 R |
| 42-8367 | 11/1967 | Japan | 260/669 R |
| 1378151 | 12/1974 | United Kingdom | 260/668 R |

Primary Examiner—Delbert E. Gantz
Assistant Examiner—Joseph A. Boska
Attorney, Agent, or Firm—Carl G. Ries; Robert A. Kulason; Carl G. Seutter

[57] ABSTRACT

Vinyl cyclohexene is converted to styrene or ethylbenzene at 170° C.–360° C. in the presence of copper chromite catalyst.

6 Claims, 1 Drawing Figure

VCH - VINYL CYCLOHEXENE
NB - NITRO BENZENE
S - STYRENE
AN - ANILINE
EB - ETHYL BENZENE

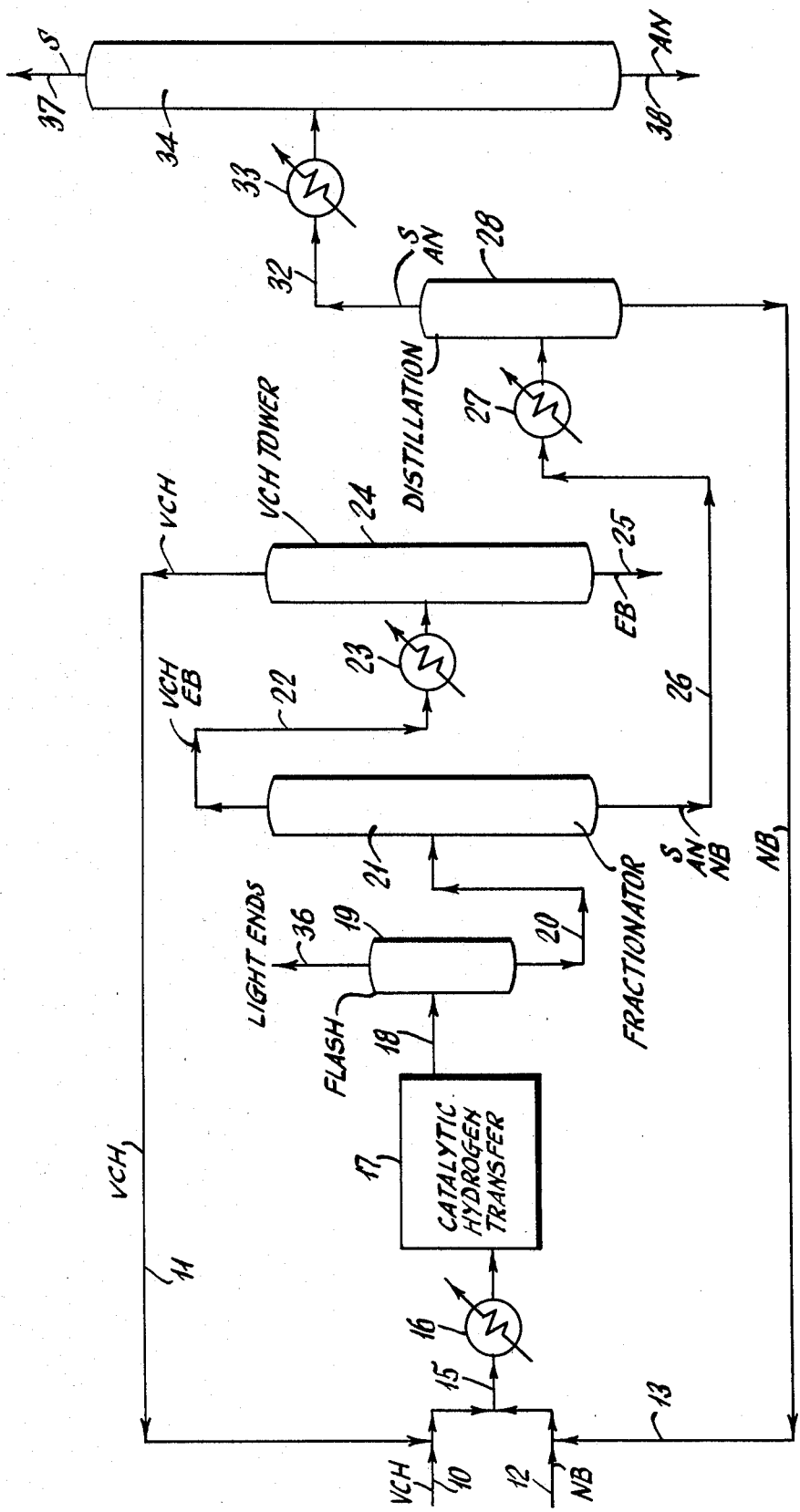

METHOD FOR PREPARING ETHYL BENZENE

This is a continuation, of application Ser. No. 952,763, filed Oct. 19, 1978, now U.S. Pat. No. 4,163,761 issued Aug. 1979.

FIELD OF THE INVENTION

This invention relates to conversion of hydrocarbons such as 4-vinyl-1-cyclohexene to aromatic products such as styrene or ethylbenzene. More particularly it relates to the use of a catalyst to effect such conversions.

BACKGROUND OF THE INVENTION

As is well known to those skilled in the art, it is possible to prepare styrene from ethylbenzene; and there are various processes for providing ethylbenzene charge. A continuing need for increased styrene production may result in increased demand for ethylbenzene. Simultaneously it is found that decreased use of butadiene in rubber compositions results in over-supply of this material; and thus there is a source of raw material which may readily be converted (by well-known processes for dimerization) to vinyl cyclohexene.

It is known (Bin Din et al., Synthesis 1978, pages 23–24) that nitro compounds may be reduced to amines in the presence of hot liquid paraffin at 360° C.–390° C.

SUMMARY OF THE INVENTION

In accordance with certain of its aspects, the novel method of this invention may comprise passing a charge stream containing vinyl cyclohexene and $R'NO_2$, wherein $R'$ is alkyl, cycloalkyl, aralkyl, aryl, or alkaryl, into contact with a catalytic amount of copper chromite as catalyst, thereby forming product stream; and withdrawing said product stream.

DESCRIPTION OF THE INVENTION

Charge hydrocarbon to the process of this invention is vinyl cyclohexene. 4-vinyl-1-cyclohexene, sometimes referred to as "butadiene dimer", may be commercially available or it may be prepared by dimerization of butadiene by well-known processes typified by that set forth at U.S. Pat. No. 2,544,808 to A. E. Staley, or *The Chemistry of Petrochemicals* by M. J. Astle (1956) page 123. Although the process of this invention may be employed to convert 2-vinyl-1-cyclohexene or 3-vinyl-1-cyclohexene to desired products, it is found that the advantages of this process may be more readily attained using, as charge, the 4-vinyl-1-cyclohexene isomer.

The charge vinyl cyclohexene may be used as recovered in impure or crude form or it may be purified. Preferably it will be free of any added stabilizers.

The process of this invention may be carried out by reacting the vinyl cyclohexene with a nitrohydrocarbon $R'NO_2$ wherein $R'$ is a hydrocarbon moiety selected from the group consisting of alkyl, cycloalkyl, alkaryl, aryl, and aralkyl.

Although it may be possible to utilize polynitro compounds such as dinitrobenzene, etc., and such compounds are included in the representation $R'NO_2$, it is more preferred to use a mononitro compound.

In the above compound, $R'$ may be a hydrocarbon radical selected from the group consisting of alkyl, cycloalkyl, aralkyl, aryl, and alkaryl, including such radicals when inertly substituted. When $R'$ is alkyl, it may typically be propyl, butyl, i-butyl, hexyls, octyls, etc. When $R'$ is cycloalky, it may typically be cyclohexyl, etc. When $R'$ is aralkyl, it may typically be benzyl, etc. When $R'$ is aryl, it may typically be phenyl, naphthyl, etc. When $R'$ is alkaryl, it may typically be tolyl, xylyl, etc. $R'$ may be inertly substituted, i.e., it may bear a nonreactive substituent such as alkyl, aryl, cycloalkyl, ether, halogen, nitro, etc. Typically, inertly substituted $R'$ groups may include p-chlorophenyl, 3-chloro-5-methylphenyl, etc. The preferred $R'$ groups may be aryl. $R'$ may preferably be phenyl.

Illustrative compounds $R'NO_2$ may include:

TABLE nitrobenzene
dinitrobenzene
p-nitrotoluene
2,4-dinitrotoluene
p-nitrochlorobenzene
1-nitropropane
p-nitroanisole
1-nitro-n-octane
3-nitrophenol
nitrocyclohexane
1,2-dinitroaniline
6-nitroquinoline
4-nitrobenzonitrile
methyl 4-nitrobenzoate The most preferred of these compounds is nitrobenzene.

In practive of the process of this invention, vinyl cyclohexene is reacted with $R'NO_2$ in the presence of copper chromite, a hydrogen transfer catalyst, at hydrogen transfer conditions. Hydrogen transfer catalysts are characterized by the ability of the catalyst system to exchange hydrogen between two molecules of different polarity.

The copper chromite, which may be employed as catalyst in practice of the process of this invention, may be characterized by the formula $0.5{-}2\,CuO.1Cr_2O_3$; and the typical commercial product which may be employed may have a ratio of 1:1, i.e., have the empirical formula $CuO.Cr_2O_3$, also written $CuCr_2O_4$.

Preferably the catalyst may be used in the form of particles having a largest dimension of 1 mm–15 mm, say 4 mm.

The process of this invention may be carried out batchwise (in an autoclave) or continuously. The reaction conditions for continuous reaction may include the following:

TABLE

| Condition | Broad | Preferred | Typical |
|---|---|---|---|
| Temperature, °C. | 170–360 | 220–300 | 260 |
| Pressure, psig | 0–500 | 0–100 | 0 |
| LHSV | 0.003–6.0 | 0.006–2.0 | 1.5 |
| Mole ratio of $R'NO_2$ to vinyl cyclohexene | 0.1–1.0 | 0.33–0.67 | 0.67 |
| Mole ratio of catalyst to vinyl cyclohexene | 0.001–0.1 | 0.002–0.005 | 0.0026 |

The reaction conditions for batch reaction may include:

TABLE

| Condition | Broad | Preferred | Typical |
|---|---|---|---|
| Temperature, °C. | 170–360 | 220–300 | 260 |
| Pressure, psig | 0–500 | 0–100 | 50 |

| Condition | Broad | Preferred | Typical |
|---|---|---|---|
| Time of Reaction, hrs. | 1–20 | 2–15 | 10 |
| Mole ratio of R'NO$_2$ to vinyl cyclohexene | 0.1–1.0 | 0.3–0.7 | 0.67 |
| Mole ratio of catalyst to vinyl cyclohexene | 0.001–0.1 | 0.002–0.005 | 0.0026 |

The reaction is typically carried out in vapor phase under atmospheric pressure in the presence of the heterogeneous catalysts.

During the course of the typical reaction, in liquid phase, hydrogen transfer occurs, the vinyl cyclohexene being dehydrogenated to produce styrene and ethylbenzene; and nitrobenzene being reduced to aniline:

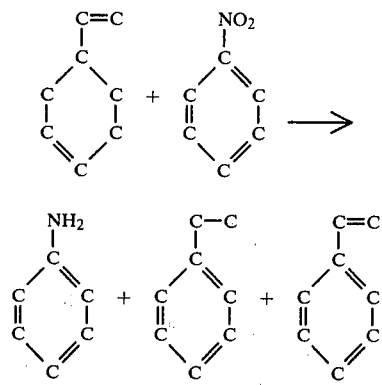

It may be desirable to carry out the reaction in the presence of a diluent-solvent which does not react under the conditions of reaction and such diluent-solvents may include hydrocarbons, preferably aromatic hydrocarbons such as benzene, xylene, toluene, etc., preferably benzene.

Reaction effluent may be particularly characterized by a high selectivity to styrene. The selectively to styrene may be 5–40, typically 10–30, say about 20 mole %.

Reaction effluent from the reaction zone is withdrawn and passed to a fractionation operation. Here there may be obtained several principal streams:

(i) a small amount of light ends (which are produced as undesired by-products) which are withdrawn as an overhead, e.g., from a preliminary flashing operation;

(ii) unreacted vinyl cyclohexene which may be recovered and recycled to the reaction zone;

(iii) product styrene plus lesser amounts of aniline, and ethylbenzene;

(iv) unreacted nitrobenzene bottoms which (optionally after separation from catalyst) may be recycled to the reaction zone; and (v) spent catalyst (which optionally may be recycled).

Clearly, the particular recovery system will depend upon the composition of the reaction effluent and the preferred product to be recovered.

DESCRIPTION OF PREFERRED EMBODIMENTS

Practice of the novel process of this invention may be apparent from the following description of a preferred embodiment wherein, as elsewhere in this specification, all parts are parts by weight unless otherwise specifically noted. The accompanying drawing represents schematically a flow sheet of one technique whereby the process of this invention may be carried out. It will be apparent to those skilled in the art that the drawing may show major pieces of equipment, and that various pumps, valves, heat exchangers, collection drums, etc. may not be shown.

EXAMPLE I

In this example, which represents practice of the process of this invention, 12.12 parts of copper chromite are charged to a catalyst bed.

A mixture (in liquid phase) of 8.1 parts (0.075 moles) of 4-vinyl-1-cyclohexene (butadiene dimer) and 6.2 parts (0.05 moles) of nitrobenzene is passed through the catalyst bed over 97 minutes. The bed is maintained at 260° C. and atmospheric pressure.

The reactor effluent is collected and analyzed. It is found that the selectivity (mole %) to styrene is 19.2% based upon vinyl cyclohexene. Selectivity to ethylbenzene, on the same basis, is 7.5%. Selectivity to aniline, based on nitrobenzene, is 3.8%.

EXAMPLE II*

In this control example, the process of Example I is duplicated except that the catalyst bed contains 13.21 parts of copper oxide CuO. No reaction occurred. The product stream was found to contain a "trace" of styrene and no ethylbenzene or aniline.

EXAMPLE III*

Results comparable to those attained in Example II may be observed if the catalyst bed contains chromic oxide Cr$_2$O$_3$.

Results comparable to those attained in Example I may be attained if the nitro compound is:

| Example | R'NO$_2$ |
|---|---|
| IV | dinitrobenzene |
| V | p-nitrotoluene |
| VI | 2,4-dinitrotoluene |
| VII | p-nitrochlorobenzene |
| VIII | 1-nitropropane |
| IX | nitrocyclohexane |

BRIEF DESCRIPTION OF THE DRAWING

The process of this invention may be carried out continuously in accordance with the schematic flow sheet shown in the drawing.

EXAMPLE X

In this embodiment, there is admitted through line 10 charge 4-vinyl-1-cyclohexene (676.4 parts) which is combined with 143.3 parts of recycle VCH from line 11. Charge nitrobenzene (284.7 parts) is added through line 12 together with 337.9 parts of recycle NB through line 13 to total 622.6 parts total charge NB. Catalyst in a bed in operation 17 is copper chromite.

Charge containing VCH, NB, and catalyst is passed through line 15 and heated in heat exchanger 16 to ca. 260° C./50 psig. The mixture is passed through reaction zone 17 at LHSV of 1.5. Reaction effluent in line 18 is flashed in flash drum 19 to yield 2.3 parts of light ends withdrawn through line 36. Flashed liquid is passed through line 20 to fractionator 21 from which overhead may be withdrawn containing 143.3 parts VCH and 50.7 parts EB. This fractionator overhead is passed through line 22 and heat exchanger 23 to VCH tower 24 from which 143.3 parts VCH is recovered and recycled through line 11. Bottoms from VCH tower 24 include 50.7 parts EB recovered through line 25.

Bottoms from fractionator 21 containing styrene, aniline, and nitrobenzene are passed through line 26 and heat exchanger 27 to distillation tower 28 from which there are recovered through line 13 bottoms containing nitrobenzene. This stream, containing 337.9 parts of nitrobenzene, is recycled to charge through line 13.

Overhead from distillation tower 28 containing 36.5 parts of styrene and 100 parts of aniline is passed through line 32 and heat exchanger 33 to rectification tower 34. Here, 31.5 parts of styrene are recovered as overhead in line 37 and 100 parts of aniline are recovered as bottoms in line 38.

Although this invention has been illustrated by reference to specific embodiments, it will be apparent to those skilled in the art that various changes and modifications may be made which clearly fall within the scope of this invention.

We claim:

1. The method for preparing ethylbenzene which comprises:

passing a charge stream containing vinyl cyclohexene and $R'NO_2$, wherein $R'$ is alkyl, cycloalkyl, aralkyl, aryl, or alkaryl, into contact with a catalytic amount of copper chromite as catalyst at 170° C.–360° C. thereby forming product stream containing ethylbenzene;

withdrawing said product stream containing ethylbenzene and recovering ethylbenzene from said product stream.

2. The method claimed in claim 1 wherein said reaction is carried out at 220° C.–300° C.

3. The method claimed in claim 1 wherein said $R'NO_2$ is nitrobenzene.

4. The method claimed in claim 1 wherein said copper chromite is characterized by the formula a $CuO \cdot Cr_2O_3$ and a is 1–2.

5. The method for preparing ethylbenzene which comprises:

passing a charge stream containing vinyl cyclohexene and nitrobenzene into contact with a catalytic amount of copper chromite as catalyst at 170° C.–360° C., thereby forming product stream containing ethylbenzene;

recovering said product stream containing ethylbenzene; and recovering ethylbenzene from said product stream.

6. The method for preparing ethylbenzene as claimed in claim 5 wherein said vinyl cyclohexene is 4-vinyl-1-cyclohexene.

* * * * *